(12) United States Patent
Richards et al.

(10) Patent No.: US 6,395,473 B1
(45) Date of Patent: May 28, 2002

(54) ADENOVIRAL BASED PROMOTER ASSAY

(75) Inventors: Karen Richards, Windmoor; Thomas H. Rushmore, Hatfield; Manal A. Morsy, Blue Bell, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/743,570

(22) PCT Filed: Jul. 9, 1999

(86) PCT No.: PCT/US99/15563

§ 371 (c)(1), (2), (4) Date: Mar. 7, 2001

(87) PCT Pub. No.: WO00/04185

PCT Pub. Date: Jan. 27, 2000

Related U.S. Application Data

(60) Provisional application No. 60/092,777, filed on Jul. 14, 1998.

(51) Int. Cl.[7] ............................ C12Q 1/68; C12Q 1/70; C12N 15/861; C12N 5/10; C12N 15/63

(52) U.S. Cl. ............................ 435/5; 435/6; 435/29; 435/320.1; 435/455; 435/456; 435/325; 435/366; 435/370; 435/371; 435/91.4; 435/91.41; 435/91.42

(58) Field of Search .................... 435/320.1, 5, 6, 435/29, 455, 456, 325, 366, 370, 371, 91.4, 91.41, 91.42

(56) References Cited

U.S. PATENT DOCUMENTS

| | | | | |
|---|---|---|---|---|
| 5,654,168 A | * | 8/1997 | Bujard et al. | 435/69.1 |
| 5,733,745 A | * | 3/1998 | Kowalski et al. | 435/69.3 |
| 6,204,060 B1 | * | 3/2001 | Mehtali et al. | 435/456 |

OTHER PUBLICATIONS

Bernard Massie et al, Inducible Overexpression of a Toxic Protein by an Adenovirus Vector with a Tetracycline–Regulatable Expression Cassette, Journal Of Virology, Mar. 1998, pp. 2289–2296.*

* cited by examiner

*Primary Examiner*—David Guzo
(74) *Attorney, Agent, or Firm*—Joanne M. Giesser; Jack L. Tribble

(57) ABSTRACT

Adenoviral vectors are used to transfer a promoter/reporter gene construct to mammalian cell cultures. The promoter/reporter gene construct is used to determine if a candidate inducing agent has promoter-inducing activity; or can be used to determine if a candidate promoter has activity in the presence of a known inducer.

16 Claims, 1 Drawing Sheet

United States Patent US 6,395,473 B1

ADENOVIRAL BASED PROMOTER ASSAY

This application claims benefit under 35 USC 119(e) of provisional application 60/092,777, filed Jul. 14, 1998.

FIELD OF THE INVENTION

The present invention relates to an assay system in mammalian cells using a recombinant adenovirus vector.

BACKGROUND OF THE INVENTION

Some drugs and drug metabolites effect a transcriptional response in key genes within the cell. Promoter/reporter assay systems are one way to examine transcriptional regulation in vitro. In general, promoter/reporter assay system join a promoter to a reporter gene whose transcriptional or translational product is known. If the promoter actually directs transcription and/or translation of the reporter gene, its transcriptional and/or translational product can be easily determined.

To date, standard plasmid vectors have been used for delivery of promoter/reporter cassettes to cells. However, traditional methods, such as lipofection, calcium phosphate precipitation, and electroporation, are cumbersome and generally inefficient delivery systems when the cells are mammalian, and in particular primary hepatocytes.

The liver is the primary site for metabolism of most drugs. The levels of several drug metabolizing enzymes in the liver are altered in response to drug exposure and in some instances this alteration is a result of transcriptional regulation. Liver cell cultures would provide a good model of drug metabolism in vivo, but liver cells are difficult to transfect efficiently.

It would also be desirable to efficiently transfect mammalian cells with foreign DNA to study promoter regulation of a gene involved in drug metabolism. It would also be desirable to obtain an assay system to examine transcriptional regulation of genes coding for a drug metabolizing enzyme in mammalian cells.

DETAILED DESCRIPTION OF THE INVENTION

The present invention relates to a method of determining if a candidate promoter is responsive to an inducing agent in a mammalian cell culture comprising:

a) constructing an adenovirus vector wherein an E1 gene region is replaced by the candidate promoter operatively linked to a reporter gene construct;

b) introducing the vector into mammalian cells;

c) contacting the cells with an inducing agent; and d) determining if the reporter gene is expressed.

The present invention further relates to a method of determining if a promoter is responsive to a candidate promoter inducing agent in a mammalian cell culture comprising:

a) constructing an adenovirus vector wherein an E1 gene region is replaced by the promoter operatively linked to a reporter gene construct;

b) introducing the vector into mammalian cells;

c) contacting the cells with a candidate inducing agent; and d) determining if the reporter gene is expressed.

In both of the methods described, there may be an optional step of quantifying the expression of the reporter gene.

In a specific embodiment, the present invention relates to a rat glutathione S-transferase Ya subunit promoter sequence linked to a reporter construct, chloramphenicol acetyltransferase (CAT).

Figure 1:
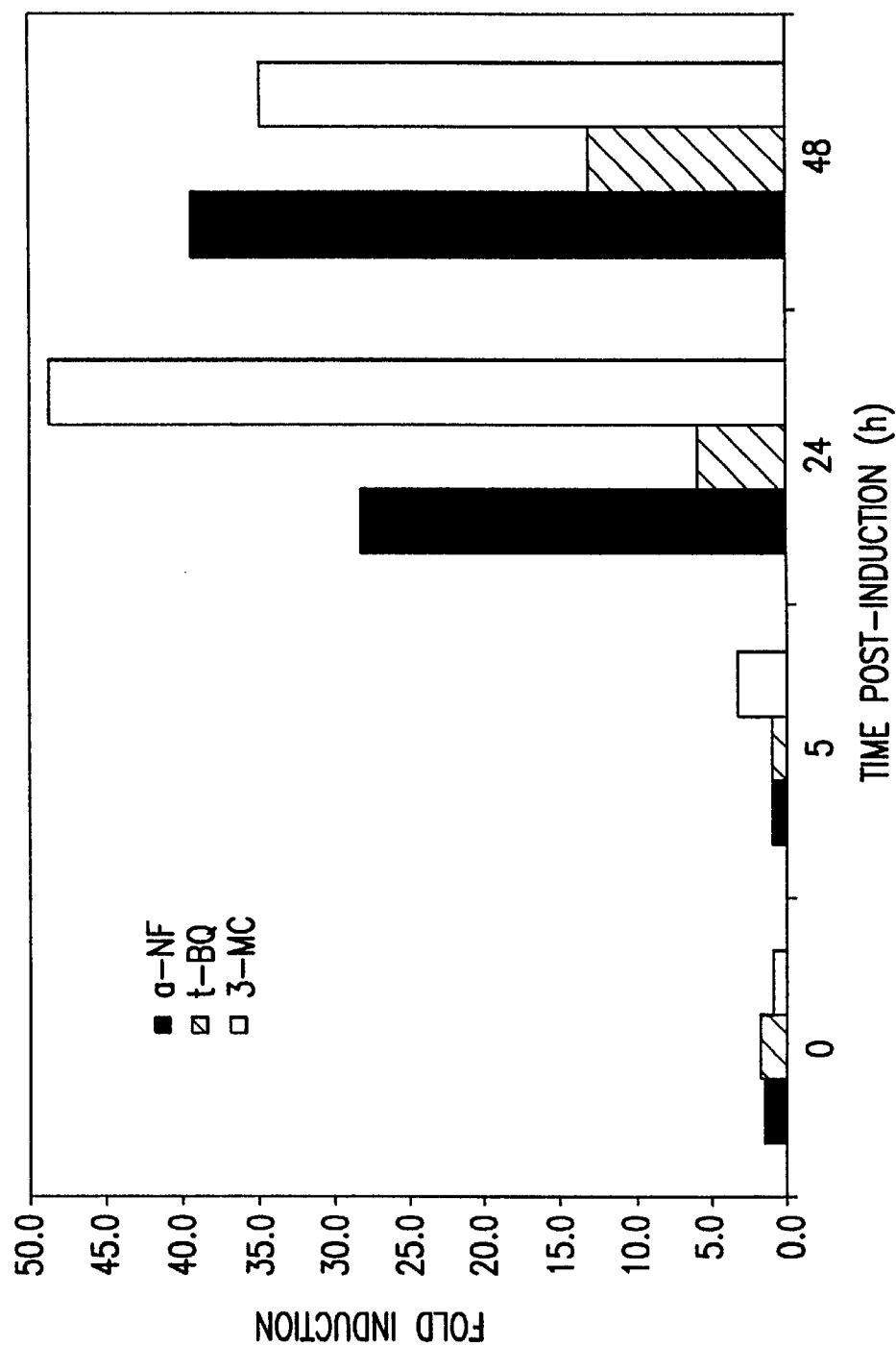
FIG. 1 is a graph showing CAT activity induced over time by a-napthoflavone (a-NF), t-butyhydroquinone (t-BQ), or 3-methylcholanthrene (3-MC)a-NF in HepG2 cells infected with Ad1.6CAT. The left bar of each data set represents a-NF, the middle bar represents t-BQ, and the right bar represents 3-MC.

As used throughout the specification and claims:

"reporter gene construct" means a gene whose transcriptional product (mRNA) or translational product (for example, protein, light, or color) is expressed in the presence of a functional promoter candidate. It includes known regulatory sequences (except for the promoter).

"Candidate promoter" means a nucleotide sequence which contains elements that control transcription.

Plasmid vectors have been used for delivery of promoter/reporter cassettes to cells. However, traditional methods for transfecting cells with such vectors are cumbersome. Further, mammalian cell lines are generally inefficient in the uptake of foreign DNA. One of the problems in the past has been that when performing an assay using transfected mammalian cell lines, the results were inconsistent due to the-variability of uptake and transformation. Thus, cell lines were not particularly good models of in vivo activity.

The present invention relates to a reliable assay method which efficiently and effectively introduces the foreign DNA into the mammalian cells through the use of an adenovirus vector.

Adenovirus vectors are generally used in gene therapy applications, but have not been used much as general delivery vectors for non-gene therapy applications. This invention takes advantages of many of the adenoviral vector characteristics—adenoviral vectors can be obtained in high titer; they have a broad host range, infecting both dividing and non-dividing cells; and they are relatively easy to manipulate using standard molecular biological techniques known in the art. The infection of the virus in mammalian cells is rapid and does not require exposure to toxic or harmful substances in contrast to previous methods of introducing foreign DNA into cells.

Adenovirus vectors of the present invention may include any adenovirus, for example serotypes 2, 5, 7, 12, and helper-dependent vectors.

There are several strategies commonly used in the art to generate recombinant adenovirus vectors, and protocols detailing these strategies are available (Degryse et al, 1996, *J. Virology* 70:4805–4810). Such strategies involve, but are not limited to, the cloning of the wild-type adenovirus genome, the insertion of a promoter upstream from the E3 region, replacement of E1 region by an exogenous expression cassette, and the deletion of the E1 region. Other regions such as E2 and/or E3 may be deleted as well. The generation of recombinant adenovirus vectors is based on the manipulation of the full-length virus genome as stable plasmid in *E.coli* and the use of the bacterial homologous recombination machinery.

In general, an adenovirus vector according to this invention will have a genome size of approximately 25 kb to approximately 36 kb. Much of the viral genome may be deleted, as long as deleted gene products are supplied in trans during viral propagation. If the deleted virus (and the inserted heterologous DNA) have a total size of less than about 25–35 kb, then it is recommended that "stuffer" DNA be added to increase the vector size. Stuffer DNA in the present invention means any non-coding DNA sequence used to increase the vector size so that it packages efficiently.

The cell lines which can be used in accordance with this invention are any mammalian cell lines susceptible to adenoviral infection. Since adenovirus can infect almost any mammalian cell line, this is intended to include numerous cell lines. Particularly of interest are human cell lines, and of most interest are hepatocytic cell lines epithelial cell lines and intestinal cell lines. This invention specifically envisions cell lines: HEPG2 Caco-2, 293, Chang liver, IEC-6, HUV-EC, IEC 16 and primary cells from rat, monkey and humans.

The liver is the primary site for metabolism of most drugs. Often, a drug or its metabolite may alter an enzymic pathway in the liver. Further, the alteration may be at the DNA transcription and/or translation level, involving the activation or suppression of a promoter. Thus in a preferred embodiment of this invention, the candidate inducing agent is a drug, a drug metabolite or an enzyme involved in drug metabolism.

One aspect of this invention is to determine if a drug or its metabolite in the environment of a liver cell will activate or suppress a known promoter. To carry out this assay, a promoter/reporter gene construct is assembled. The promoter is operatively linked to a reporter gene. Reporter genes are known in the art and include chloramphenicol acetyltransferase (CAT),β-galactosidase (β-gal), luciferase, and aequorlin secretory alkaline phosphatase (SEAP), green fluorescent protein (GFP) and enhanced blue fluorescent protein (EGFP). The adenoviral vector containing the promoter/reporter construct is introduced into the cell culture, the candidate drug (candidate promoter inducer or suppressor) is added, and the reporter gene activity is determined. This type of assay is particularly effective in investigating if a candidate drug will have undesirable side-effects.

In a related assay, a DNA sequence suspected of having promoting. activity can be assayed. Here, the candidate promoter is linked to the reporter gene construct, and a promoter inducing agent is introduced. If the DNA does possess promoting activity, then the reporter gene product will be expressed.

Yet another embodiment of this invention is a method of determining if a rat glutathione S-transferase Ya subunit promoter is responsive to an inducing agent in an HepG2 cell culture. The adenovirus of this invention comprises a rat glutathione S-transferase Ya subunit promoter sequence operatively linked to a chloramphenicol transferases (CAT) reporter gene construct, designated Ad1.6CAT. Ad1.6CAT vector was infected into HepG2 cells, supplied with a media comprising an inducing agent, such as a-NF, T-BQ, and 3-MC where the CAT activity was determined.

The following non-limiting examples are presented to better illustrate the invention.

EXAMPLE 1

Adenovirus Construction

DNA coding for a promoter/reporter rat glutathione S-transferase Ya subunit 1.6 kb promoter sequence positioned upstream of the chloramphenicol acetyltransferase reporter gene was cloned into the adenovirus shuttle vector pdelE1sp1B, whereby the E1B genome of the adenovirus is deleted and replaced. Successful construction of the shuttle vector, pdelE1sp1B-1.6CAT was verified by both restriction mapping and by sequencing across the 5'- and 3'-ends of the cloning sites. In addition, the shuttle vector was tested functionally in HepG2 cells for regulation of expression of CAT by a-napthoflavone (50 mM).

In order to construct a viable virus with the 1.6CAT DNA inserted into the adenovirus genome, a strategy based on homologous recombination in *E. coli* was used. Correct recombination was verified by restriction analysis. The virus genome thus obtained (Ad1.6CAT) was transfected into subconfluent 293 cells for plaque selection. Individual plaques were amplified and analyzed for activity. High titer virus was obtained by expansion in 293 cells and purification by triple cesium chloride banding. The viral titer was determined based on the plaque-forming units (pfu) defined in the 293 cell line.

EXAMPLE 2

Ad1.6CAT Infection of HepG2 Cells and Induction of CAT Expression

HepG2 cells were seeded in 12- or 24-well plates at a density of 60–70% confluence. Cells were infected the following day with Ad1.6CAT ($9.7 \times 10^8$ pfu/ml) at an MOI of 5 for 1 h. At the end of the infection period the virus was removed, the cells were rinsed once with PBS, and fresh media was placed on the cells. The HepG2 cells were fed with media containing a-napthoflavone (a-NF, 50 mM), t-butyhydroquinone (t-BQ, 25 mM), or 3-methylcholanthrene (3-MC, 25 mM) 24 h after infection to induce CAT expression. Control cells received media without inducer.

EXAMPLE 3

Cell Harvest and Measurement of CAT Activity

HepG2 cells were harvested at various time points following induction of CAT expression. The cells were washed with PBS, treated with trypsin/EDTA, washed again with PBS, and resuspended in lysis buffer (0.25 M Tris-Cl, pH 7.5). Cells were lysed by 3 cycles of freeze/thaw, and the lysate was clarified by centrifugation. CAT activity determined by the method of Gorman et al. using 10 ug of protein for 60 minute at 37° C. Acetylated products of chloramphenicol were extracted with mixed xylenes and quantitated by liquid scintillation counting. Results were expressed as fold induction versus control. Induction of CAT activity by a-NF in HepG2 cells infected with pdelE1sp1B-1.6CAT showed approximately 45 fold induction and approximately 85 fold induction after 24 and 48 hours, respectively. Further CAT activity is shown in FIG. 1.

What is claimed is:

1. A method of determining if a candidate promoter is responsive to an inducing agent in a mammalian cell culture comprising:
   a) constructing an adenovirus vector wherein an E1 gene region is replaced by the candidate promoter operatively linked to a reporter gene construct;
   b) introducing the vector into mammalian cells;
   c) contacting the cells with an inducing agent; and
   d) determining if the reporter gene is expressed.

2. A method according to claim 1 wherein the reporter gene is selected from the group consisting of: chloramphenicol transferases, β-galactosidase, luciferase, aquorlin secretory alkaline phosphatase (SEAP), green fluorescent protein (GFP), and enhanced blue fluorescent protein (EGFP).

3. A method according to claim 1 wherein the inducing agent is a drug or drug metabolite.

4. A method according to claim 1 wherein the mammalian cells are of human origin.

5. A method according to claim 4 wherein the human cells are liver cells, intestinal or epithelial cells.

6. A method according to claim 5 wherein the cells are selected from the group consisting of: HepG2, Caco-2, 293, Chang liver, HUV-EC, IEC-6 and IEC-18.

7. A method according to claim 1 wherein step (d) includes quantification of the expressed reporter gene product.

8. A method of determining if a promoter is responsive to an candidate promoter inducing agent in a mammalian cell culture comprising:
   a) constructing an adenovirus vector wherein an E1 gene region is replaced by the promoter operatively linked to a reporter gene construct;
   b) introducing the vector into mammalian cells;
   c) contacting the cells with a candidate promoter inducing agent; and
   d) determining if the reporter gene is expressed.

9. A method according to claim 8 wherein the reporter gene is selected from the group consisting of: chloramphenicol transferases, β-galactosidase, luciferase, aquorlin SEAP, GFP, and EGFP.

10. A method according to claim 8 wherein the candidate promoter inducing agent is a drug or drug metabolite.

11. A method according to claim 8 wherein the mammalian cells are of human origin.

12. A method according to claim 11 wherein the human cells are liver cells, intestinal cells or epitheial cells.

13. A method according to claim 12 wherein the liver cells are selected from the group consisting of: HepG2, Caco-2, 293, Chang liver, HUV-EC, IEC-6 and IEC-18.

14. A method according to claim 8, wherein step (d) includes quantification of the expressed reporter gene.

15. The method of claim 8 wherein the promoter is a rat glutathione S-transferase Ya subunit promoter.

16. A method of determining if a candidate promoter is responsive to an inducing agent in a mammalian cell culture comprising:
   a) constructing an adenovirus vector wherein an E1 gene region is replaced by a promoter sequence coding for a rat glutathione S-transferase Ya subunit operatively linked to a chloramphenicol acetyltransferase-reporter gene, said vector designated Ad1.6CAT;
   b) introducing Ad1.6CAT vector into a HepG2 cell;
   c) supplying the mammalian cell with a media comprising an inducing agent; and determining if the reporter gene is expressed.

* * * * *